United States Patent
Santus et al.

(12)

(10) Patent No.: US 6,214,386 B1
(45) Date of Patent: Apr. 10, 2001

(54) PROMPT-RELEASE ORAL PHARMACEUTICAL COMPOSITIONS FOR EXTEMPORANEOUS SUSPENSIONS

(75) Inventors: Giancarlo Santus, Milan; Roberto Golzi, Cremona, both of (IT)

(73) Assignees: Recordati, S.A.; Chemical and Pharmaceutical Co., Chiasso (CH)

( * ) Notice: Subject to any disclaimer, the term of this patent is extended or adjusted under 35 U.S.C. 154(b) by 0 days.

(21) Appl. No.: 08/754,855

(22) Filed: Nov. 22, 1996

Related U.S. Application Data

(60) Provisional application No. 60/008,936, filed on Dec. 20, 1995.

(30) Foreign Application Priority Data

Nov. 22, 1995 (IT) .............................................. MI95A2427

(51) Int. Cl.$^7$ ...................................................... A61K 9/16
(52) U.S. Cl. ........................ 424/498; 424/490; 424/493; 424/494; 424/495; 424/497
(58) Field of Search .................................. 424/490, 498, 424/497, 493, 495, 494

(56) References Cited

U.S. PATENT DOCUMENTS

| 4,764,375 | 8/1988 | Paradissis . |
| 5,296,236 | 3/1994 | Santus et al. . |
| 5,460,828 | 10/1995 | Santus et al. ........................ 424/489 |

FOREIGN PATENT DOCUMENTS

| 0068450 A2 | 1/1983 | (EP) . |
| 0273890 A1 | 7/1988 | (EP) . |
| 0 608 850 A1 | 8/1994 | (EP) . |

OTHER PUBLICATIONS

International Search Report for PCT/EP96/05127.

*Primary Examiner*—Fred Zitomer
(74) *Attorney, Agent, or Firm*—Darby & Darby

(57) ABSTRACT

A pharmaceutical composition suitable for preparing an extemporaneous suspension, that promptly releases active agents or ingredients (drugs) is disclosed. These compositions comprise an active agent in microgranule form. The microgranules containing the active agent are coated with a film coating mixture containing at least one lipid material and an optional hydrophilic additive. The coating envelopes the microgranules but does not impart a controlled release property to the composition, and affords prompt release thereof once ingested.

34 Claims, No Drawings

PROMPT-RELEASE ORAL PHARMACEUTICAL COMPOSITIONS FOR EXTEMPORANEOUS SUSPENSIONS

This patent application is based on Provisional patent application Ser. No. 60/008,936, filed on Dec. 20, 1995. Applicants claim the benefit of the filing date of the aforesaid Provisional application under 35 U.S.C. §119(e)(1). Applicants also claim priority under 35 U.S.C. §(a–d) of Italian patent application No. MI95A 002427, filed Nov. 22, 1995.

FIELD OF THE INVENTION

The present invention concerns a pharmaceutical composition suitable for preparing an extemporaneous suspension, that promptly releases active agents or ingredients (drugs). These compositions and the extemporaneous suspensions prepared with them are suitable for oral administration.

BACKGROUND OF THE INVENTION

Suspensions are heterogeneous systems in which the continuous phase (external phase) is liquid or semisolid, while the dispersed phase (internal phase) consists of solid particles that are insoluble in the medium used. Pharmaceutical suspensions can be prepared during the industrial production phase (ready-to-use suspensions), or prepared by the patient at the time of use (extemporaneous suspensions).

Suspensions are one of the most versatile of the pharmaceutical forms that can be used for administration. Suspensions are suitable for internal or external delivery of active agents, such as oral, injectable, and dermatologic uses.

The use of suspensions for the administration of active ingredients has been known for some time, and ready-to-use oral suspensions are usually preferred in everyday practice. This preference is due to the fact that the patient must simply agitate the bottle prior to use, because the continuous liquid phase is already present in the bottle. Extemporaneous suspensions, however, require the patient to first redisperse the powdered drug in a solution such as water.

Examples of "ready-to-use" suspensions on the market include BACTRIM®, a syrup with antibacterial action, and MAALOX®, a suspension with antacid action used to treat epigastric pain.

U.S. Pat. No. 4,764,375 discloses crystals of soluble active agents that are incorporated into melted waxes, and the formation of extemporaneous suspensions with or without the addition of surfactants. Further, waxes have been used to coat tablets, principally to mix with powders, or for granulation in the melted state. In addition, waxes have been used to form wax matrices of tablets or granulated materials, for the purpose of obtaining controlled-release formulations, *Pharm. Acta Helv.*, 56 4/5, 111 (1981).

European Patent application 608,850 (EP 608,850) discloses formation of microgranulated materials having characteristics such that they can easily be suspended in aqueous solutions after film-coating. However, the disclosed preparation of these suspensions in quantity, with standard, consistent and repeatable, characteristics, is typically influenced by a large number of variables, for example the density of the internal and external phases; the ratio of the phase volumes; the viscosity of the external phase; and the dimensions, degree of aggregation, and shape of the particles. The variability of these parameters can cause difficulties during resuspension, even after agitation at the time of use. In some cases the resuspension difficulties can lead to a nonhomogeneous distribution of the active agent.

In addition, currently available suspensions can have certain limitations which make them poorly suitable for use. This can occur, for example, when a problem exists with the instability of the vehicle or palatability of the suspended form, such as when an active agents with unpleasant organoleptic characteristics are used, or when mutually incompatible active agents are combined in the same formulation.

Reduction or elimination of these drawbacks often involves taking additional measures such as masking the organoleptic characteristics of active agent, or isolating it from the ingestion medium. This is frequently accomplished by microencapsulation. However, this often requires the employment of solvents and in a process that is costly.

Another drawback of masking by microencapsulation is the delaying action that the encapsulating substances can exert at the time of release of the active agent. In some cases this delaying effect has been used specifically to modulate the release of the drug according to a predetermined profile. For example, U.S. Pat. No. 5,296,236 discloses microgranular controlled-release suspensions for oral use which have the peculiarity of gradually releasing various types of active agents over time, thus adapting them to the various desired therapeutic conditions.

A delay in the release of the active agent is not always desirable or necessary for the administration of certain active agents such as, for example, analgesics, antipyretics, antitussives, and the like.

Another advantage of suspensions is their particular ease of swallowing especially when compared to solid pharmaceutical forms. This is a typical characteristic of liquids. This is particularly important in pediatrics, for the elderly, and patients suffering from motor coordination impairment, such as stroke victims, who can have difficulties swallowing tablets.

The need for a solution to this problem is epitomized by the continuing search for devices making it easy to crush a tablet to produce a powder that can be dispersed in water. For example, International Patent Applications WO 95/6427 and WO 95/6428 have recently described devices, a syringe and superimposed cups, capable of crushing tablets and the subsequent resuspension of the resultant powder in water. These devices have obvious limitations, for example, in the presence of poorly palatable active agents. In addition, the excipients of the tablets are not normally those most suitable for promoting suspension of the crushed tablet.

Thus there is a particular need for drugs that are readily available in suspended form, and, when necessary, for the ability to mask the taste of these drugs. Many active agents possess palatability problems. It is well known, for example, that acetaminophen, a very common analgesic and antipyretic, has a bitter and metallic taste that makes it difficult to administer by means of liquid formulations, particularly to children. Other examples include of Naproxen ((+)6-Methoxy-α-methyl-2-naphthaleneacetic acid), a well-known anti-inflammatory known to depart an intense burning sensation in the mouth; diltiazem, a cardiovascular drug having a strongly bitter taste; and moguisteine a bitter-tasting antitussive with anesthetic properties. Some drugs such as diltiazem are unstable in aqueous solution. Thus, it is advantageous to have available an extemporaneous suspension that has good stability as well as a pleasant taste.

There is also a need for formulations that control the hygroscopicity of certain substances. For example, it is known from the literature that potassium bicarbonate can be used to prevent osteoporosis and hypertension, *New Engl. J.*

Med. 330, 1251, 1776 (1994), and U.S. Pat. No. 5,171,583. However, this salt has tolerability and hygroscopicity problems. Thus, the ability to provide a pharmaceutical form which can overcome these drawbacks without delaying the release of the active agent constitutes a suitable solution to the problem.

An object of the present invention is to provide pharmaceutical formulations for use in a liquid suspension for oral use which, allows prompt release of the active agent, and avoids the aforementioned problems that are encountered with common ready-to-use suspensions. The present compositions are simple and inexpensive to prepare and their preparation readily lends itself to scale-up on a commercial scale.

SUMMARY OF THE INVENTION

The present invention provides a composition for prompt-release of an active agent, and a liquid suspension comprising the composition and a liquid carrier. The composition comprises an active agent in microgranule form. The microgranules containing the active agent are coated with a film coating mixture containing at least one lipid material and an optional hydrophilic additive. The coating envelopes the microgranules but does not impart a controlled release property to the composition, and affords prompt release thereof once ingested.

The inventors have found that film-coating with lipid (including wax) materials, applied in the melted state and optionally in the presence of hydrophilic additives, as wetting agents, provide formulations suitable for such suspensions, particularly extemporaneous suspensions. Such formulations can mask the taste of an active agent or ingredient (drug) and improve its stability characteristics. Further, liquids containing an active agent in the form of microgranules of reduced dimensions even when coated with lipid material, are easier to swallow.

In addition, the microgranules can be formed into tablets that can be administered without water. Thus, there is no need of reconstitution. The patient itself provides the fluid, e.g., saliva.

DESCRIPTION OF THE PREFERRED EMBODIMENTS

All patents, patent applications, and literature references cited in the specification are hereby incorporated by reference in their entirety. In the case of inconsistencies, the present disclosure, including definitions, will prevail.

The subject invention provides a prompt-release pharmaceutical composition for administration of an active agent (drug) or ingredient. The composition comprises an active agent coated with a film coating that can be extemporaneously suspended in a liquid.

The active agent is in microgranule or microparticle form. The microgranules are coated with a film forming composition comprising a mixture comprising at least one lipid material and optionally an hydrophilic additive.

Any active agent or ingredient (drug) which is suitable for administration via an oral suspension can be used in the practice of the present invention. Non-limiting examples of active agents include drugs such as, for example, diltiazem, ibuprofen, moguisteine, naproxen, acetaminophen, potassium bicarbonate, sodium bicarbonate, diphenhydramine hydrochloride diphenhydramine citrate, prednisone, fluoxetine, fluconazole, paroxetine, ketoprofen, dextromethorphan hydrobromide, and the like.

The present invention thus includes a prompt-release therapeutic system dosable in liquid form comprising:

1) prompt-release form of an active agent, having dimensions comprised between 50 and 500 $\mu$m, able to easily remain in suspension in a liquid, including:
   (i) an active agent optionally suitably transformed by means of excipient into a microgranular nucleus (microgranules);
   (ii) a film coating(s) enveloping the microgranular nucleus for the purpose of forming a barrier insensitive to taste. The barrier, provides prompt-release of the active agent (drug) contained in the nucleus and, at the same time, prevents premature dissolution in the liquid suspension and masks taste. The coating is thin so that it does not appreciably enlarge the size of the coated granules, thereby assuring stability in suspension and convenience of swallowing;
   (iii) an optional additional hydrophilic coating overlaying the first, which, while keeping the dimensions of the granules in the predetermined limits, promotes dispersibility of the coated microgranules in the liquid carrier, when suspended in the liquid vehicle.

2) A liquid carrier (vehicle system) which can be an aqueous vehicle. If desired, the liquid carrier can be extemporaneously constituted from a dry mixture by adding water. The dry mixture may contain such optional desirable ingredients as suspending agents, sweetening agents and thickening agents to impart rheological characteristics to the suspension that promote its stability.

In addition to the active agent, the pharmaceutical compositions of the invention can include suitable granulation excipients, such as hydrophilic additives within the microgranules, to aid dissolution upon ingestion. Other conventional excipients can also be added. The hydrophilic additives are typically a minor portion of the microgranules.

The terms microgranules or microparticles as used herein refer to particles typically range in size from about 50 to about 500 $\mu$m. The preferred size range is from about 100 to about 300 $\mu$m. The active agents are typically converted into microgranular form according to the procedure described in European Patent application 608,850 (EP 608,850) and U.S. Pat. No. 5,460,828. In the present invention, it is desirable to have available microgranulated materials with morphological characteristics suitable both for subsequent coating and for producing a good suspension.

Without being bound to theory, it is believed that when the active agent is present in homogeneous form, with crystals of regular shape with no sharp angles, a lipid material (including wax) can applied directly onto the crystals of active agent. However, crystals of regular shape with no sharp angles, are relatively rare and may be encountered only in a few situations. The present invention, overcomes this problem by permitting the active agent to be prepared in microgranular form, thus making the coating process applicable to any active agent regardless of its crystalline and morphological characteristics. It is thus possible to coat crystals of the active agent directly.

The present invention comprises coating of the microgranules of an active agent a with film of a lipid material in the melted state. The coated microgranules can readily form a suspension by simply adding a suspending liquid (suspending phase). Thus, the suspension can be easily reconstituted by a patient immediately before use.

The liquid suspension of the present invention allows prompt (rapid) release of the active agent, after only a few minutes. As defined herein, rapid or prompt release means that the pharmaceutical composition will release no more than about 10% of said active agent within 1 minute of mixing the film coated microgranules with the liquid carrier and at least 75% of the active agent within 45 minutes. Specifically, release occurs within about 60 minutes from reconstitution, depending on the solubility of the active agent in the liquid carrier. In addition, the preparations can be provided with good flavor masking. It is thus possible to have mixtures of different active agents in suspension without release of the active agents being substantially influenced by the other materials in the composition.

The suspensions of the invention can mimic the ingestion conditions of a film-coated tablet which typically requires from about 30 to about 60 minutes before the active agent is solubilized and absorbed. The average percentage dissolution of a tablet is estimated by many pharmacopeias to be equal to about 75% within a 45 minutes. (See U.S. Pharmacopeia XXIII, p. 1925.)

To avoid a delaying effect on release of the active agent from the lipid material applied, the lipid material is spray-deposited onto the microgranulated material itself in layers of varying thickness depending on the solubility of the active agent. However, none of the layers will cause a delay in the release of the active agent.

The pharmaceutical composition of the invention can have a weight percent of coating mixture of from about 1 to about 25 percent, and preferably from about 5 to about 20 percent, with respect to the weight of the microgranules containing the active agent. The active agent comprises from about 10 percent to about 95 percent of the weight of the film coated microgranules. Preferably the active agent will be from about 20 percent to about 80 percent of the total weight of the microgranule.

In principle, any technique known in the art can be used for coating microgranules. Some of these, however, have disadvantages.

The film coating can be applied to the microgranules in a melted state. The preferred method for film coating the microgranules of the present invention with lipids, is coating the microgranules in a fluidized-bed such as the WURSTER® system, *Pharm. Res* 7, (11), 1119 (1990). In this system, the coating material is sprayed through a nozzle onto the microgranules that are suspended by a stream of air in a cylinder. After exposure to the coating material, the particles are allowed pass to an expansion chamber, and to drop to the bottom of the device to begin a new film-coating cycle.

The inventors have also discovered that melted-wax technology can be adapted to coating of microgranules. The microgranules can be coated with a layer of wax or lipid material in a controlled manner, using only preheated compressed air as the atomization fluid following the method described in U.S. patent application Ser. No. 08/452,435. The molten materials are atomized in the desired quantity, without the aid of any solvent, and coated onto the microgranulated material containing the active agent.

The microgranules are introduced in a Glatt fluid bed apparatus provided with a 1.2 mm nozzle and the apparatus is preheated to about 35° C. The coating materials) is (are) sprayed, feeding the nozzle with a peristaltic pump, keeping a constant flux and nebulizing by means of air injected at a pressure generally of about 2 to about 4 Bar, and preferably at about 3 Bar. Once the coating with the first solution is terminated, if desired, coating of successive layers using the same or different film coating materials are performed in a similar way. If desired, the coating with film forming materials may be repeated several times. When the coating of the last layer is completed, the coated granulate is allowed to cool and dry, which may be conveniently accomplished by keeping it in the Glatt apparatus at 40° C. for about 30 minutes, after which the coated product is ready.

Typically, lipids are first melted by incubation at a temperature of about 110° C. They are then sprayed in the melted state at a temperature of about 80° C., onto the microgranules. This is accomplished using air pre-heated at a temperature of about 125° C. and compressed to a pressure of about 3 bar using a coaxial nozzle which mixes the melted wax and the hot compressed air. The spraying step is performed with a 7" WURSTER® insert in a Glatt apparatus. Wax amounts equivalent to about 10% by weight (relative to the weight of the uncoated microgranules) are sprayed at a rate of about 1.5 g/min.

The preferred lipid materials for coating the microgranules are those which are able to release the active agent or ingredient after 1 minute (about 10% or more of product released), and is nearly complete within 45 minutes (about 75% or more of product released).

Non-limiting examples of lipid materials suitable for practicing the present invention are: monoglycerides, diglycerides, or triglycerides, such as, for example, monostearin, dipalmitin, tristearin, hydrogenated castor oil, and the like; $C_6$–$C_{36}$ Fatty acids and alcohols, such as, for example, stearic acid, cetyl alcohol, stearyl alcohol and the like; esters of propylene glycol, such as, for example, propylene glycol monostearate, and the like; esters of sucrose, such as, for example, sucrose monostearate, and sucrose monopalmitate, and the like; waxes, such as, for example, beeswax, candelilla wax, carnauba wax, and the like or mixtures thereof. Preferably, the waxy coating(s) is (are) applied in the melted state (i.e., without the use of solvents), by using heated compressed air as a spray medium under conditions that do not melt the microgranular core.

Other methods for coating the microgranules include methods such as, for example, coating in rotating tanks. This technology cannot, however, be applied successfully to coating microgranulated materials having dimensions between 100 and 300 μm, due to problems of agglomeration of the particles being coated. Microencapsulation technology, has been successfully applied to the coating of active agents (U.S. Pat. No. 4,822,619). However, the method disclosed in this patent requires the use of solvents and is difficult and complex to perform.

It is well known that lipid materials, in addition to being hydrophobic, exhibit poor soluble in most common organic solvents usable in the pharmaceutical field. Preferred solvents are chlorinated solvents, such as, for example, chloroform, dichloroethane, carbon tetrachloride, and the like. However, due to toxicological and environmental concerns this is not the preferred method.

Lipid materials are well known to be hydrophobic, thus, suspending microgranulated materials coated only with such materials in a polar or aqueous external phase could exhibit poor wetability in a liquid vehicle, which interferes with suspension of the particles. For example, the microgranulated material may tend to float or to adhere to the walls of the reconstitution container. These wetability problems can be solved by using a layer comprising a hydrophilic material coated over the lipid material(s) or by addition of a hydrophilic material to the film forming lipid material(s).

The preferred process for applying the hydrophilic wetting material is to incorporate the hydrophilic material into the film to be deposited onto the microgranules containing the active agent.

Non limiting examples of suitable hydrophilic materials for use with the lipid materials are hydrophilic polymers, such as, for example, cellulose acetophthalate, hydroxypropylmethylcellulose, polyethylene glycol, and the like; ionic surfactants such as, for example, dioctyl sodium sulfosuccinate, sodium lauryl sulfate, and the like; nonionic surfactants such as, for example, partial esters of fatty acids and anhydrides such as for example, sorbitol (Span) or their adducts with polyoxyethylene chains (Tween) and the like.

The amount of hydrophilic material desirable for practicing the present invention ranges from about 0.1 percent to about 5 percent by weight of hydrophilic material based on the lipid coating material. The preferred range is from about 0.5 percent to about 2 percent. The amount of polymer must not be so high as to create any gastrointestinal problems such as resistance to absorption or adversely affect the release control beyond the desired limits.

After coating, the microgranules containing the active agent can be formulated with optional excipients useful for the preparation of the vehicle system, which can be reconstituted with the external (liquid) phase prior to use. Non-limiting examples of additives for the vehicle include; suspending or structuring agents such as, for example, cellulose esters, microcrystalline cellulose, alginic acid derivatives, polyvinylpyrrolidone derivatives, and the like; sugars, as the substrate of the said vehicle, such as, for example, sucrose, sorbitol, xylitol, dextrose, mannitol, and the like; buffering compounds such as, for example, citric acid, sodium citrate, sodium phosphate, potassium phosphate, and the like; flavors and edulcorants such as, for example, saccharine, aspartame, and flavors commonly used in the pharmaceutical sector. The vehicle can also include substances to reinforce the taste, such as citric acid, sodium chloride, and the like.

The mixture intended for suspension can be distributed into various dosage forms for reconstitution with an appropriate external phase, liquid carrier, by the patient. A particularly useful form is a single-dose packet, generally consisting of a paper/aluminum/polyethylene laminate. Laminates having 10 g/m² paper, aluminum at a thickness of 10 to 20 $\mu$m, and 30 g/m² polyethylene can be used for packets.

Another single-dose dosage form consists of reservoir-stopper vials. These have the advantage that the vehicle is already present in the liquid phase contained in the bottle, while the coated microgranular particles are stored in the reservoir stopper. The user, after removing a protective ring, can breach the reservoir stopper causing the microgranules to mix with the liquid vehicle.

For administering active agents which require multiple doses, a dosage form can be prepared which comprises a multi-dose bottle containing a mixture of coated microgranules and a vehicle. The user can measure out the solid coated microgranules, and reconstitute the necessary quantity of suspension.

In addition, the coated microgranules can be formed into dosage unit forms such as tablets such as lyophilized tablets and the like. These can be administered with or without water. Thus, there is no need for reconstitution. The patient itself provides the fluid (saliva or gastrointestinal fluids). These tablets disperse the coated microgranules rapidly when added to an aqueous solution. It has also been found that the inclusion of an effervescent mixture in the lyophilized tablet is particularly useful. The effervescence further reduces the sand effect of the microgranules.

The ingredients usually employed in the preparation of the tablets include excipient materials like those described hereinabove and also include: mannitol, dextrins, sugars, etc. as diluents in presence of a binders such as, for example gelatin or polyvinylpyrrolidone (PVP), and the like. Flavoring agents and edulcorants can also be added to these materials.

Materials suitable for preparing an effervescent mixture are bicarbonates and organic acids such as citric or tartaric acid and the like. The effervescent tablets are then lyophilized in presence of organic solvents, such as: dioxane, t-butyl alcohol, and the like.

The amount of time required to release the active agent was assessed by dispersing the coated microgranulated material, in water, then sampling the solution at different times. The samples were analyzed to determine the amount of active agent it contained. The microgranulated material was coated with lipid material so that during the time needed to reconstitute it with water (approximately a minute) there was minimal release of active agent, and that the release was complete after about 45 minutes. Thus, the invention avoids the slow- or delayed-release phenomena.

EXAMPLES

The following examples illustrate the invention without limitation.

Example 1

Microgranular Formulation of Potassium Bicarbonate 2 kg of potassium bicarbonate was mixed with lactose and polyvinylpyrrolidone K 30 (BASF Corp., Mount Olive, N.J.) and wet with 100 ml of water in a Fielder P25 granulator. After adding the water and granulating for 10 minutes, the granulated material was dried and sieved until a particle fraction having dimensions between 100 $\mu$m and 300 $\mu$m was obtained. A mixture of lipids having the following composition was applied onto the granulated material:

| Component | % (w/w) |
|---|---|
| Beeswax | 8 |
| Glyceryl monostearate | 90 |
| Cetyl alcohol | 1 |
| Stearyl alcohol | 1 |

The lipids were maintained in a melted state, at a temperature of approximately 110° C., and sprayed to coat the microgranules using compressed air preheated to a temperature of 125° C. and at a pressure of 3 bar. The spraying process is performed with a 7" WURSTER® insert on a Glatt GPCG 3 apparatus. The spraying apparatus was maintained at approximately 80° C. The quantity of lipid material was equal to 15% w/w with respect to the granulated material. It was sprayed at a rate of 2.5 g/min. In the final phase of the coating process, sodium lauryl sulfate in a quantity equal to 1% of the weight of the lipids used was dispersed in the melted lipids. The microgranulated material coated in this manner exhibited good dispersibility in water.

Example 2

Tasteless, Prompt-Release Microgranular Compositions of Diltiazem

Following the method described in Example 1, a microgranulated material having the following composition was prepared:

| Component | Weight (g) |
|---|---|
| Micronized diltiazem hydrochloride | 600 |
| Micronized lactose (MICROTOSE ®) | 2100 |
| Polyvinylpyrrolidone K30 | 300 |

After drying, the fraction of microgranules having dimensions between 125 and 300 µm was separated by sieving. A Glatt GPCG 3 apparatus with a 7" WURSTER insert and 1.2 mm nozzle was used to apply a composition consisting of the same mixture of components in two different formulations (I and II):

| Component (%) | Formula I (%) | Formula II |
|---|---|---|
| Glyceryl monostearate | 90 | 49 |
| White wax | 8 | 49 |
| Cetyl alcohol | 1 | 1 |
| Stearyl alcohol | 1 | 1 |

The lipid components were melted at a temperature greater than about 80° C., and were sprayed with a pump having a flow rate of 3.2 g/minute and an atomization pressure of 3 bar, using compressed air preheated to a temperature of 120° C.

Nine coating tests (A–I) were performed. The percentage of the coating material and the respective percentage of surfactant (dioctyl sodium sulfosuccinate—DSS) used for each sample is indicated in Table 1.

TABLE I

| | A | B | C | D |
|---|---|---|---|---|
| Formula I | 10% | 15% | 20% | 20% |
| DSS | — | — | — | 0.2% |

| | E | F | G | H | I |
|---|---|---|---|---|---|
| Formula II | 5% | 10% | 15% | 20% | 20% |
| DSS | — | — | — | — | 0.2% |

In formulations D and I, the surfactant was calculated with respect to the waxes and was added directly into the lipid material at the end.

Example 3

Dissolution Tests on Formulations Containing Diltiazem

The dissolution of the active agent in formulations (A–I) from Example 2 was determined in accordance with the procedure cited in U.S. Pharmacopeia XXIII, p. 1791. A 1.2 gram sample of the coated microgranules were added to 900 ml of distilled water. Aliquots of 1 ml of solution were taken at 1 minute, 30 minutes, and 45 minutes. respectively and analyzed spectrophotometrically at a wavelength of 240 nm.

TABLE II

| | % DILTIAZEM RELEASED | | | | | | | | |
|---|---|---|---|---|---|---|---|---|---|
| Time | A | B | C | D | E | F | G | H | I |
| 1' | 3.2 | 0.2 | 0 | 2 | 26 | 2.7 | 2 | 0.3 | 2 |
| 30' | 100 | 91 | 93 | 98 | 100 | 75 | 36 | 15 | 83 |
| 45' | 100 | 100 | 95 | 99 | 100 | 98 | 78 | 52 | 100 |

The data in Table II show that percentage of the diltiazem detected in the solutions for each of the formulations analyzed. These results show that the coatings of the invention rapidly release the active agent.

Example 4

Preparation of Single-Dose Packets of Prompt-Release Diltiazem

Microgranules, 3.45 kg, coated according to formulation B of Examples 2 and 3, were mixed with a vehicle consisting of:

| Component | Weight (kg) |
|---|---|
| Mannitol | 5 |
| Polyvinylpyrrolidone | 0.5 |
| Lemon flavor | 0.5 |
| Citric acid | 0.9 |
| Precipitated silica | 0.05 |
| Sucrose to make | 30 |

The resultant mixture was measured into 10,000 3-gram packets, each containing 60 mg of diltiazem hydrochloride, using a Marchesini packing machine. The composition of each packet was 30 g/m² paper, 12 µm aluminum, and 40 g/m² polyethylene.

Example 5

Microgranulating Acetaminophem to Mask Taste

Following the method described in Example 1, a microgranulated material having the following composition: 50% acetaminophen, 40% lactose, 10% polyvinylpyrrolidone (PVP K30) was prepared. After granulation with water, drying, and sieving over a 0.6 mm mesh, the fraction between 100 and 300 µm was separated. The resulting microgranules were coated under the conditions described in Example 2 using a lipid mixture containing 80% glyceryl monostearate and 20% carnauba wax. The coated granulated material was then mixed with a vehicle and packed into packets with the following composition:

| Component | Weight (g) |
|---|---|
| Coated acetaminophen | 0.550 (equal to 0.250 g of acetaminophen) |
| Polysorbate 80 | 0.01 |
| E 110 coloring | 0.0016 |
| Citric acid | 0.1 |
| Orange flavor | 0.10 |
| Orange powder | 0.60 |
| Caraway flavor | 0.003 |

-continued

| Component | Weight (g) |
|---|---|
| Precipitated silica | 0.01 |
| Powdered sugar to make | 3 |

The polysorbate 80 was absorbed onto the precipitated silica before being mixed with the other excipients of the packet.

Example 6

Prompt-Release Suspension of Naproxen with Taste Masking

Following the method described in Example 1 a microgranules having the following composition: 3200 g micronized naproxen, 400 g polyvinylpyrrolidone (PVP K30), 400 g lactose, and 30 g polyethylene glycol (PEG 6000) were prepared. After mixing for 5 minutes, 500 ml of water was added by spraying at 2 bar with agitation, and the mixture was mixed for another 15 minutes until the microgranules formed spheroids. The microgranules were dried in a static oven to a residual moisture of between 4 and 5% by weight for 2 hours at 35° C. A 0.6 mm sieve was used to separate the fraction of microgranules between 90 and 300 μm. A lipid mixture having the following composition (Formula III) was applied to the granulated material:

| | |
|---|---|
| Glyceryl monostearate | 90% |
| Beeswax | 8% |
| Cetyl alcohol | 1% |
| Stearyl alcohol | 1% |

Six coating tests (L–P) were performed. The percentage of coating material and the respective percentage of surfactant (METHOCEL® E15LV) added where applicable is indicated in TABLE III, below. The METHOCEL® was sprayed after dissolving it in an 80:20 mixture of methanol and water.

TABLE III

| | L | M | N | O | P | Q |
|---|---|---|---|---|---|---|
| Formula III | 5% | 10% | 10% | 10% | 10% | 15% |
| METHOCEL ® E15LV | — | — | 1% | 2% | 3% | — |

Example 7

Dissolution Tests for the Formulations Containing Naproxen

Following the method described in Example 3, the dissolution of formulations L-Q was performed, using a pH 7.4 phosphate buffer as the medium. The results were recorded spectrophotometrically, absorption at 330 nm. The results are in Table II below.

TABLE IV

| | % NAPROXEN RELEASED | | | | | |
|---|---|---|---|---|---|---|
| Time | L | M | N | O | P | Q |
| 1' | 0.3 | 0.2 | 0.2 | 0.5 | 0.5 | 0.5 |
| 30' | 56 | 29 | 40 | 48 | 50 | 22 |
| 45' | 75 | 55 | 63 | 80 | 85 | 40 |

The data in Table IV show the percentage of Naproxen detected in solution for each of the formulations analyzed. These results show that the coatings of the invention rapidly release the active agent.

Example 8

Prompt-Release Suspension of Ibuprofen with Taste Masking, For Pediatric Use

Microgranules having the following composition: 400 g of micronized ibuprofen, 500 g of lactose, and 100 g of polyvinylpyrrolidone were prepared by mixing for 5 minutes and granulation with 210 ml water for 20 minutes. The mixture was then dried at 40° C. in a fluidized bed for 10 minutes to a residual relative moisture of approximately 5% by weight. The fraction of microgranules between 100 and 300 μm was separated, and a lipid composition consisting of STEROTEX®, a hydrogenated castor oil, was applied. The final film-coating phase had 1% polyethylene glycol (PEG 6000) added. The microgranules coated in this manner were measured into the reservoir stopper of single-dose vials having as vehicle an 8-ml solution having the following composition:

| | |
|---|---|
| Sorbitol | 3500 mg |
| Avicel | 50 mg |
| Orange flavor | 50 mg |
| Citric acid | 15 mg |
| Sodium benzoate | 10 mg |
| Water to make | 8 ml |

Before use, the microgranular contents of the reservoir stopper (100 mg ibuprofen) were brought into contact with the liquid in the vial, and after agitation could be readily taken by the patient.

Example 9

Extemporaneous Suspension of Moguisteine with Taste Masking

A mixture consisting of 50% moguisteine, 10% polyvinylpyrrolidone (PVP K30), and 40% lactose, was mixed in a Fielder P25 kneader/granulator. An aqueous solution of 5% polyethylene glycol (PEG 6000), corresponding to about 1% of the weight of the above mixture, was added to the mixture at a rate of 25 ml/min, using a 0.8 mm nozzle and a spray pressure of 2 bar. Kneading proceeded for approximately 20 minutes at a speed of about 200 rpm. The granulated material was allowed to form spheroids for an additional 15 minutes and allowed to dry. The microgranules were separated by sieving, and the fraction with dimensions between 100 and 300 μm was collected. The microgranules were coated with a lipid mixture having the following composition:

| | |
|---|---|
| Glyceryl monostearate | 90% |
| Beeswax | 8% |
| Cetyl alcohol | 1% |
| Stearyl alcohol | 1% |

Dioctyl sodium sulfosuccinate, 1% by weight (with respect to the mixture), was added to this mixture during the final spraying phase by dispersion into the melted mass. The weight of the coating mixture was about 5% of the weight of the microgranulated material being coated. The coated microgranulated material was mixed with a vehicle wherein each packet had the following composition:

| Component | Weight (mg) |
|---|---|
| Microgranule moguisteine | 430 (equal to 200 mg moguisteine) |
| AVICEL ® RC 591 | 500 |
| Ammonium glycyrrhizate | 50 |
| Fruit flavor | 50 |
| Sucrose to make | 3000 |

Example 10

Lyophilized Tablet

Tablets having the following composition: coated placebo granules 50 mg, gelatin 40 mg, Mannitol 30 mg, aspartame 0.5 mg, citric acid 3.5 mg, and water 480 mg, are prepared as follows:

Gelatin is dissolved in water heated to 60° C. Mannitol, citric acid and aspartame are added until solubilization is complete. The coated granules are added until an homogeneous suspension is obtained. The mixture is placed in blister packets (12), having a size of approximately 6 mm and a total weight of about 600 mg. Lyophilization is performed by freezing at about −40 to about −45° C. for 2–3 hours, then gradually raising the temperature up to about 25° C. under a vacuum of about 0.2–0.25 mbar. After lyophilization is complete, the blister is sealed with an aluminum foil.

Example 11

Effervescent Tablet

Following the method described in Example 10, a formulation having the following composition is prepared: naproxen coated granules (prepared in Example 6) 357 mg, sodium bicarbonate 52 mg, lactose 103.5 mg, saccharose 155 mg, ascorbic acid 52 mg, sodium saccharinate 2.64 mg, flavor 12 mg, PVP K30, 65.86 mg, and t-butyl alcohol, 800 mg.

The sodium bicarbonate, lactose, saccharose, ascorbic acid and sodium saccharinate are sieved to obtain particles having dimensions of about 100 μm. The components are added to PVP solubilized in t-butyl alcohol. The coated microgranules of naproxen are suspended in the mixture. The mixture is then suspended in blister packets and lyophilized as described in Example 10.

The invention has been described above by reference to preferred embodiments but, as those skilled in the art will appreciate, many additions, omissions and modifications are possible all within the scope of the claims below.

What is claimed is:

1. A prompt-release pharmaceutical composition for administration of an active agent, said composition comprising:
   an active agent in the form of microgranules having a spheroidal form which does not present sharp or discontinuous surfaces allowing upon coating of said microgranules a uniform formation of film wherein said microgranules are coated with a film coating comprising a mixture of at least one lipid material and optionally, a hydrophilic additive;
   wherein said coating envelops said microgranules but does not impart a controlled release property to said composition when added to a liquid carrier, wherein said coating comprises from about 1 to about 25 percent of said pharmaceutical composition by weight.

2. The pharmaceutical composition according to claim 1, wherein less than about 10% of said active agent is released within 1 minute of mixing in water and that at least 75% of said active agent is released within 45 minutes of mixing in water at 37° C.

3. The pharmaceutical composition according to claim 1, wherein said active agent is selected from the group consisting of diltiazem, ibuprofen, moguisteine, naproxen, acetaminophen, sodium bicarbonate, potassium bicarbonate, diphenhydramine hydrochloride, diphenhydramine citrate, prednisone, fluoxetine, fluconazole, paroxetine, ketoprofen, dextromethorphan hydrobromide, and mixtures of the foregoing.

4. The pharmaceutical composition according to claim 3, wherein said active agent comprises from about 10 percent to about 95 percent by weight of said microgranules.

5. The pharmaceutical composition according to claim 4, wherein said active agent comprises from about 20 percent to about 80 percent by weight of said microgranules.

6. The pharmaceutical composition according to claim 3, wherein said active agent is a mixture of at least two active agents.

7. The pharmaceutical composition according to claim 1, wherein said microgranules comprise an active agent and suitable granulation excipients.

8. The pharmaceutical composition according to claim 7, wherein said granulation excipients contained in said microgranules are selected from the group consisting of dibasic calcium phosphate, lactose, microcrystalline cellulose, starch, talc, sugars, polyvinylpyrrolidone, polyvinylpyrrolidone-vinyl acetate copolymer, sodium phosphate, citric acid, and tartaric acid.

9. The pharmaceutical composition according to claim 1, wherein said microgranules have a diameter of from about 50 to about 500 μm.

10. The pharmaceutical composition according to claim 9, wherein said microgranules have a diameter of from about 100 to about 300 μm.

11. The pharmaceutical composition according to claim 1, wherein said lipid material comprising said film coating is selected from the group consisting of monoglycerides, diglycerides, triglycerides, fatty acids, fatty alcohols, propylene glycol esters, sucrose esters, and waxes.

12. The pharmaceutical composition according to claim 11, wherein said lipid materials are fatty acids or fatty alcohols and are predominantly saturated.

13. The pharmaceutical composition according to claim 11, wherein said lipid material is selected from the group consisting of monostearin, dipalmitin, tristearin, hydrogenated castor oil, stearic acid, cetyl alcohol, stearyl alcohol, propylene glycol monostearate, sucrose monostearate, sucrose monopalmitate, beeswax, candelilla wax, and carnauba wax.

14. The pharmaceutical composition according to claim 1, wherein said hydrophilic additive in said film coating is a hydrophilic polymer or a surfactant.

15. The pharmaceutical composition according to claim 14, wherein said hydrophilic additive is selected from the group consisting of cellulose acetophthalate, hydroxypropylmethylcellulose, dioctyl sodium sulfosuccinate, sodium lauryl sulfate, polyethylene glycol, partial esters of fatty acids, anhydrides of sorbitol, and adducts of sorbitol anhydrides with polyoxyethylene chains.

16. The pharmaceutical composition according to claim 1, wherein said film coating is applied in a melted state.

17. The pharmaceutical composition according to claim 1, wherein said film coating comprises from about 5 to about 20 percent of said pharmaceutical composition by weight.

18. The pharmaceutical composition according to claim 1, wherein the weight of said hydrophilic additive in said film coating is from about 0.1 percent to about 5 percent of the weight of said lipid coating material in said film coating.

19. The pharmaceutical composition according to claim 18, wherein the weight of said hydrophilic additive in said film coating is from about 0.5 percent to about 2 percent of the weight of said lipid coating material in said film coating.

20. A dosage unit form comprising a pharmacological composition according to claim 1, and pharmaceutically acceptable vehicle.

21. The dosage unit form according to claim 20, wherein said dosage unit form is selected from the group consisting of single-dose packets, reservoir-stopper vials, and tablets.

22. The dosage unit form according to claim 21, wherein said dosage unit form is a single-dose packet.

23. The dosage unit form according to claim 21, wherein said dosage unit form is a reservoir-stopper vial.

24. The dosage unit form according to claim 21, wherein said dosage unit form is a tablet.

25. The dosage unit form according to claim 24, wherein said tablet is an effervescent tablet.

26. A method for delivering an active agent, said method comprising, administering to a mammal in need of said active agent a composition according to claim 1.

27. The method according to claim 26, wherein said composition comprises at least one active agent selected from the group consisting of diltiazem, ibuprofen, moguisteine, naproxen, acetaminophen, sodium bicarbonate, potassium bicarbonate, diphenhydramine hydrochloride, diphenhydramine citrate, prednisone, fluoxetine, fluconazole, paroxetine, ketoprofen, dextromethorphan hydrobromide, and a mixture of any of the foregoing.

28. The method according to claim 27, wherein said composition comprises a mixture of active agents.

29. A liquid suspension comprising a prompt-release pharmaceutical composition for administration of an active agent, said composition comprising:

a) an active agent in microgranule form, wherein said microgranules have a spheroidal form which does not present sharp or discontinuous surfaces allowing upon coating of said microgranules a uniform formation of film wherein said microgranules are coated with a film coating comprising a mixture of at least one lipid material and, optionally, a hydrophilic additive;

wherein said coating envelops said microgranules but does not impart a controlled release property to said composition; wherein said coating comprises from about 1 to about 25 percent of said pharmaceutical composition by weight; and b) a liquid carrier.

30. The dosage unit form according to claim 24, wherein said tablet is a lyophilized tablet.

31. The prompt-release pharmaceutical composition of claim 1, wherein said liquid carrier is an aqueous vehicle.

32. The liquid suspension of claim 29, wherein said liquid carrier is an aqueous vehicle.

33. The composition of claim 1 wherein said microgranules have a diameter of about 50 micrometers to about 500 micrometers prior to coating.

34. The composition of claim 1 wherein the microgranules are enveloped by said coating regardless of the solubility, hydrophilicity, hydrophobicity or lipidicity of the active agent.

* * * * *